(12) United States Patent
Magana

(10) Patent No.: US 6,645,211 B2
(45) Date of Patent: Nov. 11, 2003

(54) ORTHOPEDIC SUPPORT SYSTEM AND METHOD OF INSTALLATION

(75) Inventor: Ignacio Magana, Palm Beach Gardens, FL (US)

(73) Assignee: Howmedica Osteonics Corp., Allendale, NJ (US)

( * ) Notice: Subject to any disclaimer, the term of this patent is extended or adjusted under 35 U.S.C. 154(b) by 202 days.

(21) Appl. No.: 09/778,179

(22) Filed: Feb. 7, 2001

(65) Prior Publication Data

US 2002/0107524 A1 Aug. 8, 2002

(51) Int. Cl.[7] .............................................. A61B 17/56
(52) U.S. Cl. ....................................................... 606/72
(58) Field of Search .............................. 606/60, 61, 72, 606/74, 103, 228, 233; 623/17.11, 17.15, 17.16

(56) References Cited

U.S. PATENT DOCUMENTS

| 4,146,022 | A | * | 3/1979 | Johnson et al. ............. 606/103 |
|---|---|---|---|---|
| 5,312,410 | A | | 5/1994 | Miller et al. |
| 5,573,286 | A | | 11/1996 | Rogozinski |
| 5,628,756 | A | * | 5/1997 | Barker, Jr. et al. .......... 606/139 |
| 5,681,310 | A | | 10/1997 | Yuan et al. |
| 5,989,256 | A | * | 11/1999 | Kuslich et al. .............. 606/103 |
| 5,997,542 | A | * | 12/1999 | Burke ........................... 606/61 |
| 6,050,998 | A | * | 4/2000 | Fletcher ...................... 606/103 |
| 6,093,190 | A | * | 7/2000 | Mattchen ...................... 606/74 |
| 6,093,205 | A | * | 7/2000 | McLeod et al. ............... 606/61 |
| 6,436,123 | B1 | * | 8/2002 | Magovern ................... 606/216 |
| 2002/0019634 | A1 | * | 2/2002 | Bonutti ......................... 606/60 |

FOREIGN PATENT DOCUMENTS

EP        0 322 334 A1     8/1988

* cited by examiner

Primary Examiner—Eduardo C. Robert
(74) Attorney, Agent, or Firm—Lerner, David, Littenberg, Krumholz & Mentlik, LLP

(57) ABSTRACT

A tensioned cord (208) formed into a closed loop is secured to adjacent bone structures (201, 203), and a flexible patch (236) is secured to the cord in tension so that the combined, predetermined tension is applied between the adjacent bones structures (201, 203). The tensioned cord (203) and patch (236) may be used with or without a fusion implant device (206) in order to, in the former instance, contribute to compressive forces applied to the fusion device by the surrounding bone structures. The patch (236) may also be used as a delivery medium for a substance such as bone graft (241).

55 Claims, 6 Drawing Sheets

ORTHOPEDIC SUPPORT SYSTEM AND METHOD OF INSTALLATION

TECHNICAL FIELD

The present invention relates generally to devices for implantion into the body in order to connect bone structures and, more specifically, to synthetic ligaments for joining adjacent bone structures such as vertebral bodies in order to promote healing or fusion through relative compression of bone or implant structures.

BACKGROUND OF THE INVENTION

Certain orthopedic procedures require that adjacent or nearby bone structures be placed in compression against each other to provide support, to promote fusion, or to promote healing generally. While such procedures often rely on the natural tension of surrounding soft tissues, muscles and ligaments, it is sometimes desirable to introduce cable or wire, or other structures, to apply and maintain compression between such bone structures. In instances such as intervertebral fusion, for example, where a disc space is relatively large in the vertical dimension, natural tension is hindered due to ligamentous laxity and, as a result, contact between bone and a fusion device necessary to promote good fusion is diminished.

In various medical procedures wires or cables are used to join or support body structures, such as bone structures or implant structures. Metal or synthetic wires and cables are joined at their ends using surgical knots or connecting devices such as crimping members. Various known cable tensioner devices may be employed to attain desired tensioning in loops formed by tied or crimped wires and cables, and to facilitate safe and efficient procedures.

In certain procedures such as intervertebral repair or fusion, and in instances where an implant may be utilized, it is difficult to efficiently install an effective wire or cable system that safely and precisely maintains a desired positioning and support of the bone or implant structures. This is particularly true when the repair or fusion is effected from the anterior side.

In other types of medical procedures where stability with controlled movement is needed, such as in the treatment of scoliosis, there is a need for a non-cumbersome device that supports adjacent bone structures in relation to each other while allowing a predetermined amount of relative movement.

Another problem in fusion procedures is the invasion of the desired fusion space by fibrous ingrowths which block the fusion path.

It is desired, therefore, to provide system for applying compressive forces to bone structures to promote healing or fusion, to protect a fusion space from inadvertent invasion by non-fusion structures, and to address additional shortcomings inherent therein.

OBJECTS OF THE PRESENT INVENTION

It is an object of the present invention to provide an orthopedic tensioning device for supporting adjacent bone structures relative to each other.

It is a further object of the present invention to provide an orthopedic cable system designed for efficient and safe installation and secure and precise maintenance of bone or implant bodies in precise positions and with selectively desired force. It is a further object of the present invention to provide means for protecting a fusion space from inadvertent blockage, while still enabling penetration by fusion material. These and other objects of the invention that are inherent and advantageous are disclosed herein.

SUMMARY OF THE INVENTION

In a preferred embodiment, the present invention cable system and method of installation are directed to a synthetic anterior intervertebral ligament ("S.A.I.L."). The S.A.I.L. system is utilized for joining adjacent vertebral bodies between which one or more intervertebral fusion implants have been inserted via an anterior approach. The system comprises a cable, preferably of an ultra-high molecular weight polyethylene fiber, that is tied or otherwise fastened between two intervertebral bodies having one or more fusion devices implanted therebetween. The cable is tied in such a manner as to span the gap between the intervertebral bodies in which the one or more fusion devices reside. The technique of tying the cable and the optional use of additional tensioner devices are employed to achieve desired tension. Because of the nature of the vertebral bodies' geometry on the anterior side, the present invention system and method contemplate forming one or more holes on each of the vertebral bodies to serve as loop holes through which the cable can pass to secure each vertebral body.

A patch or tube of mesh or other type of fabric, as will be described below, may be positioned and tensioned across the gap in order to add evenly distributed tension and to prevent the one or more fusion devices from migrating, particularly in a direction perpendicular to the vertebral column. The patch or tube also prevents inadvertent invasion of a fusion space by non-fusion bodies or structures, while enabling fusion growth therein. The patch or tube also provides means for holding bone graft material or bone morphogenic protein to facilitate and direct fusion growth. Selective positioning of bone graft material could be utilized to encourage the development of a sentinel sign fusion.

Another aspect of the present invention relates to utilization of a single strand of cable and/or a patch or tube that span a plurality of bone structures, such as vertebrae, in order to allow a controlled tension to be applied while allowing predetermined relative movement. Such a system can be implemented in, for example, the treatment of scoliosis. The patch or tube in that instance may be one or a plurality used in series.

DESCRIPTION OF THE PREFERRED EMBODIMENTS

Figure 1:
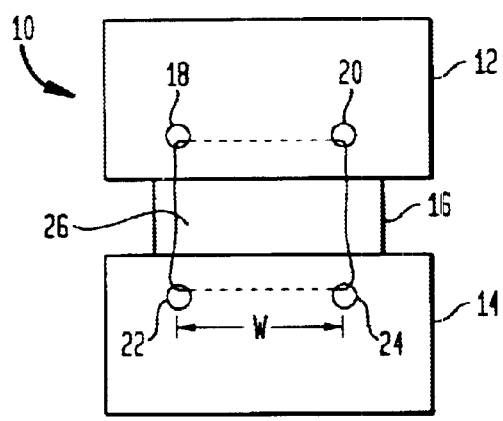
FIG. 1 is schematic view of a cord component of the present invention secured to two bone structures.

Referring to FIG. 1, a schematic representation (10) of two vertebral bodies (12, 14) in a spinal lumbar region is shown as viewed from the anterior side. Positioned between the vertebral bodies (12, 14) is an intervertebral fusion device (16). The fusion device (16) may comprise one or more of any of various known fusion devices such as bone dowels or cylindrical cages such as the Ray TFC™ cage sold by Surgical Dynamics Inc. of Norwalk, Conn. The fusion device may, for example, be comprised of a pair of cylindrical cages positioned side by side between the vertebral bodies (12, 14).

In accordance with the present invention, a pair of holes (8, 20, 22, 24) are provided on each vertebral body (12, 14), respectively, to facilitate guiding and tensioning of a cable (26). The cable (26), preferably, is made from an ultra-high molecular weight polyethylene fiber, such as the SecureStrand™ Cable System available from Surgical Dynamics Inc. of Norwalk Conn. The holes (18–24) are selectively located close to the edge of each respective vertebral body (12, 14) that is closest to the gap (28) in which the fusion device (16) resides in order to facilitate effective tensioning. The holes (18–24) on each vertebral body (12, 14) are spaced far enough apart from each other by the distance (w) as illustrated in FIG. 1, to provide evenly distributed tension across the gap (18) and to stabilize each vertebral body (12, 14) against inadvertent rotation or lateral movement.

Figure 2A:
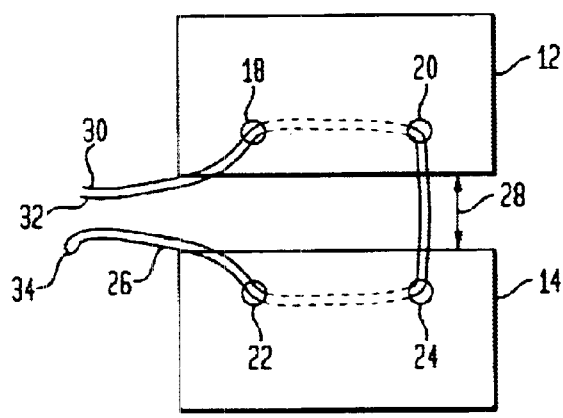
FIGS. 2A–2B are schematic views of the cord component in FIG. 1 showing opened and closed loop positions.
Figure 2B:
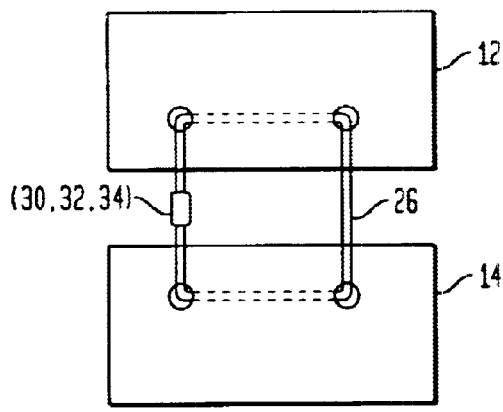

In a preferred mode of the present invention, the cable (26) comprises a single, continuous cable which is folded over, as shown in FIG. 2A, and threaded through each hole (18–24) so that the free ends (30, 32) emerge from a first hole (18) and the folded section emerges from a second hole (22) so that the emerging sections (30, 32, 34) can be tied or joined together as shown in FIG. 2B. While the embodiment of FIGS. 2A–2B shows the free ends (30, 32, 34) being positioned between holes (18, 22) on adjacent vertebral bodies, it is contemplated that the free ends (30, 32, 34) may be positioned at any location between any of the holes (18–24).

The preferred method of tying or joining the cable ends for the embodiment described in FIGS. 2A–2B is described now with reference to FIGS. 3A–3D.

Figure 3A:
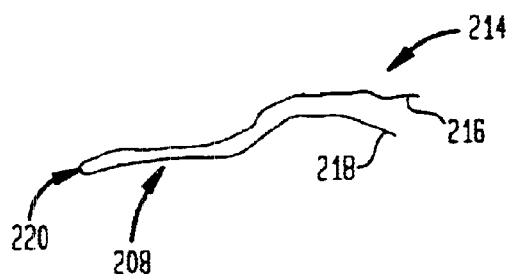
FIG. 3A is a schematic view of a cord folded according to the present invention.
Figure 3B:
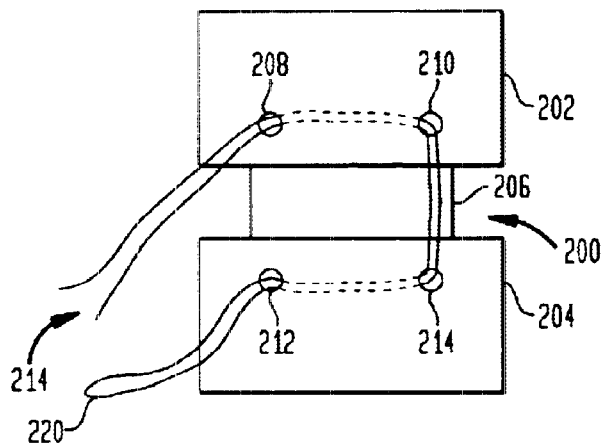
FIG. 3B is a schematic view of a cord as that shown in FIG. 3A shown secured through adjacent bone structures.

Referring now to FIGS. 3A–3B, after preparing a site for insertion of an intervertebral device using an anterior approach according to procedures known to those skilled in the art, a disc space (200) is cleared between adjacent vertebral bodies (202, 204) and a gap is maintained therebetween for insertion of a fusion device (206). A plurality of holes (208–214) are formed on each of the adjacent vertebral bodies (202, 204), on the anterior face of each (as shown in the anterior view FIGS. 3A–3B). The holes are formed using instruments and procedures known to those skilled in the art.

After placing a desired fusion device (206) into the gap or disc space (200), a cable (208) is folded as shown in FIG. 3A so that a first end (214) having two free cable ends (216, 218) and a second end (220) in the form of a folded cable section are formed.

Preferably beginning with the folded, second end (220) the cable (208) is threaded successively through holes (208–214) in a manner resulting in the configuration shown in FIG. 3B so that the cable (208) extends across the gap (200) in which the fusion device (206) resides. The cable (208) is tightened by drawing the first end (214) toward the second end (220) until the vertebral bodies (202, 204) are positioned relative to each other as desired and a desired tension in the cable (208) is achieved. The first and second ends (214, 220) are then tied or crimped.

Figure 4A:
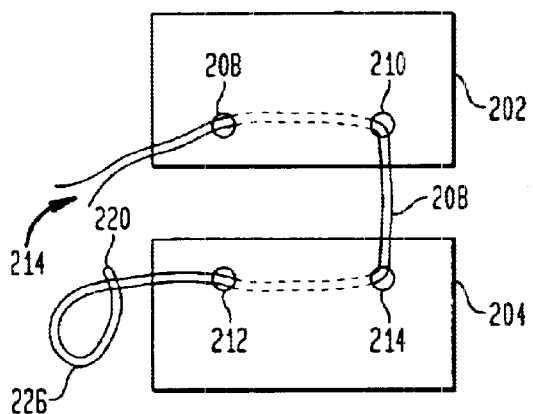
FIGS. 4A–4D are schematic views of a cord according to the present invention being positioned and secured with respect to adjacent bone structures.
Figure 4B:
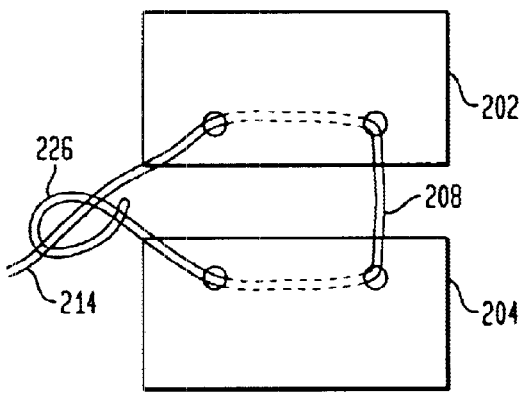
Figure 4C:
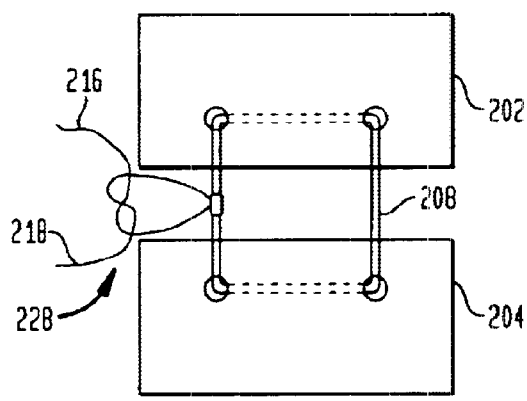
Figure 4D:
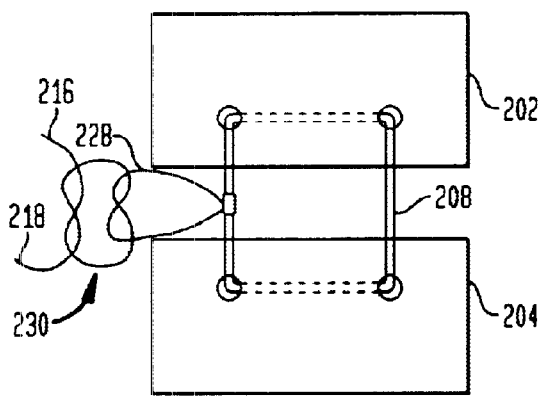

A preferred method of tying the first and second ends (214, 220) is described herein with respect to FIGS. 4A–4D. Beginning with the first and second ends (214, 220) positioned as indicated in FIG. 3B, the second end (220) having a folded cable section is positioned into a configuration known as a rocking hitch (226) as shown in FIG. 4A. Next, the first end (214) having two free cable ends is pulled through the loops formed by the rocking hitch (226) as shown in FIG. 4B. After the first end (214) is pulled through the rocking hitch (226) to a desired tension, a half-hitch (228) is formed as shown in FIG. 4C. Next, a square knot (230) is formed as shown in FIG. 4D and advanced toward the half-hitch (228) until tightened. The loose ends (216, 218) remaining after the square knot (230) is formed can be pulled away from each other for further tensioning of the square knot (230) in order to tighten the entire loop formed by the cable (208). One or more additional square knots may be formed successively with the loose ends (216, 218) to secure the tensioned cable (208) against loosening.

While the preferred method and configuration of tying the cable (208) are described above, it is contemplated that a variety of known knots or crimping members may be used to achieve a similarly closed, tensioned loop of cable.

Figure 5A:
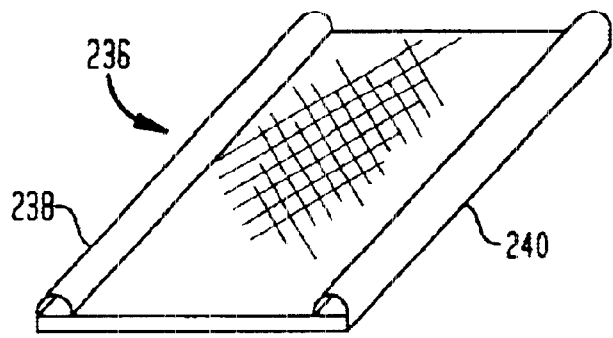
FIG. 5A is a schematic, isometric view of a flexible patch according to the present invention.
Figure 5B:
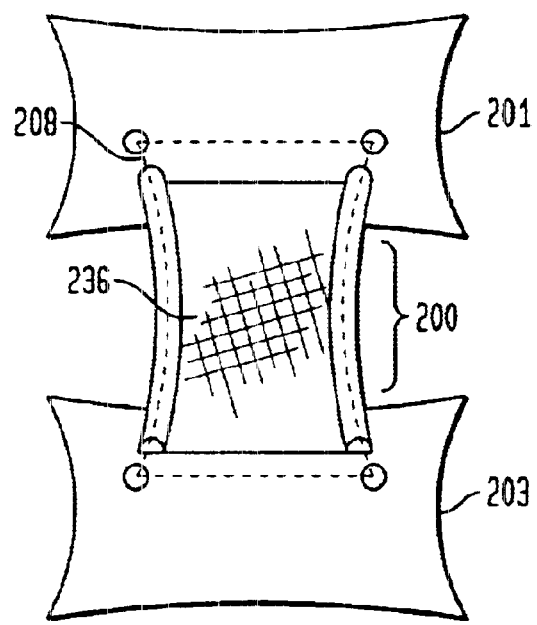
FIG. 5B is a schematic view of a flexible patch and cord according to the present invention being secured in tension between adjacent bone structures.
Figure 5C:
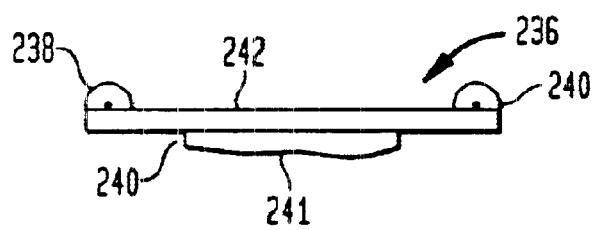
FIG. 5C is a schematic, end view of the patch and cord shown in FIG. 5C.

Another aspect of the present invention is described herein with respect to FIGS. 5A–5B. A patch (236) as shown in FIG. 5A made of fabric or a flexible material may be positioned across the anterior side of the gap (200) between adjacent vertebrae (201, 203) in a manner in which it cooperates with the cable (208) to enhance the overall tension and strength of the cable assembly to stabilize the vertebral fusion site. The patch (236) may be provided with two folds (238, 240) on opposite sides forming channels so that the cable (208) may be threaded therethrough as shown in FIG. 5B. The size of the patch (236) is selected so that the cable (208) is subjected to additional tension due to deliberate tensioning and stretching of the patch (236). Thus, the cable (208) is shown biased into arcuate shapes at its sides in FIG. 5B. It is contemplated that the cable (208) may be threaded through perforations (not shown) formed in the patch of by other means such as a hook or eyelet. The patch (236) may be made from a biocompatible or dissolvable material, including surgical mesh as illustrated in FIGS. 5A–5B. It is desirable that the material is flexible so that it can be tensioned between the cable (208) sections as shown in FIG. 5B. The inner surface (240) of the patch (236) spanning the gap (200) may be used to hold bone graft material (241) as shown in FIG. 5C, or another desired substance, or to form a barrier. Depending on the desired use, the inner surface (240) may be made from a specific material or treated in order to have desirable properties for a specific performance purpose, such as the slow release of a substance. The opposite surface (242) may also be treated and may differ from the inner surface (240).

Figure 6A:
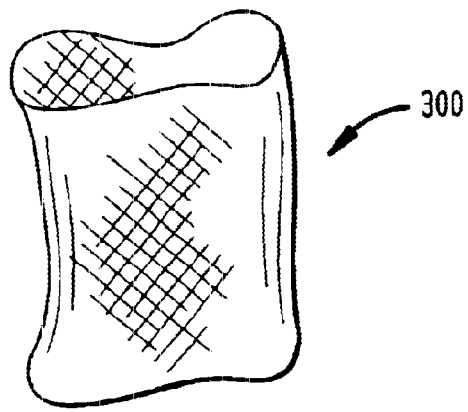
FIG. 6A is a schematic view of a tube-shaped, flexible patch according to the present invention.
Figure 6B:
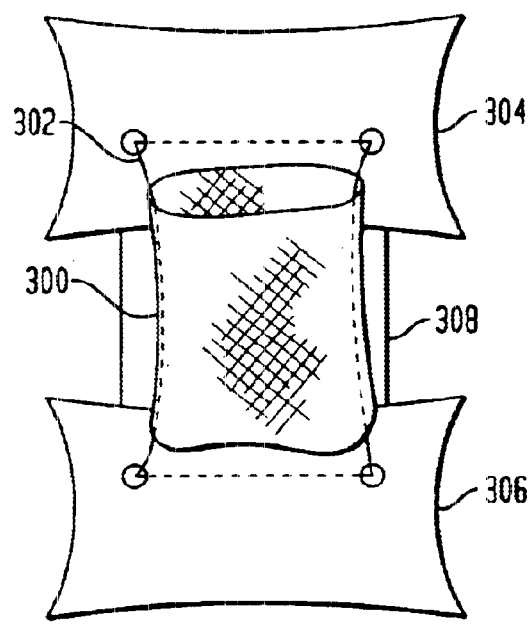
FIG. 6B is a schematic view of the tube-shaped patch of FIG. 6A and a cord secured to adjacent bone structures according to the present invention.
Figure 6C:
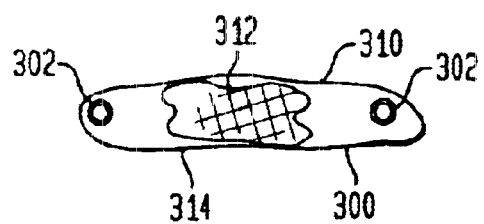
FIG. 6C is a schematic, end view of the patch and cord shown in FIG. 6B.

Referring now to FIGS. 6A–6C, there is disclosed a patch (300) configured as a tube so that it may be threaded over a cable (302) tensioned, as described with respect to the embodiments above, between adjacent vertebrae (304, 306). The sizing of the patch (300) is selected to impart tension in the patch (300) and the cable (302), causing the cable spans to deform into arcuate shapes on the sides of the patch (300) as shown in FIG. 6B. The patch (300) and cable (302) span across a gap between the adjacent vertebrae (304, 306) and across an intervertebral implant (308) such as a fusion device. The material of the patch (300) may may be selected or treated in order to have various desirable characteristics and properties such as, for example, the ability to slowly release a substance in a controlled manner or to form a barrier. A substance (310) to be released may be placed inside the tubular patch (300) as shown in FIG. 6C. The front (312) and back (314) surfaces may be designed with different characteristics and properties from each other to achieve desired performance.

Figure 7A:
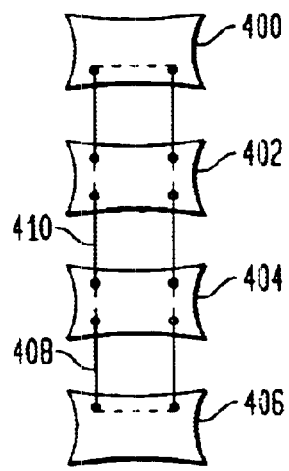
FIGS. 7A–7C are schematic illustrations of a plurality of vertebrae secured to each other with a cord in accordance with the present invention.
Figure 7B:
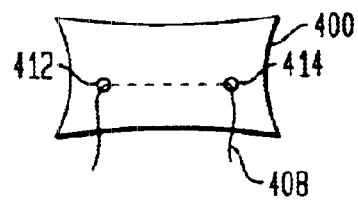
Figure 7C:
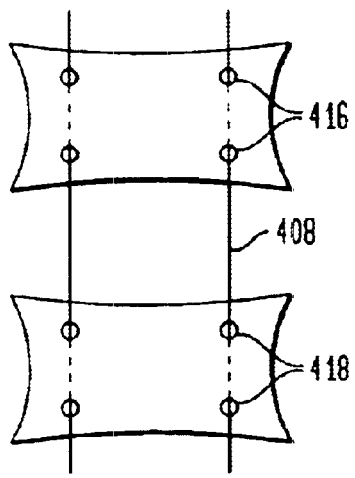

In situations where it is desirable to provide controlled tension to a plurality of adjacent vertebrae while permitting a predetermined amount of movement, a plurality of vertebrae may be joined by a single strand of cable in a manner similar to that described above, as illustrated in FIG. 7A. Referring to FIG. 7a, first, second, third and fourth vertebrae (400–406) are joined by a single cable (408) which is selectively tied or crimped at a suitable location (410) in a manner similar to that described with reference to FIGS. 4A–4D. The first (400) and last (406) vertebrae are each provided with two holes for receiving the cable (408), as shown by way of example with respect to the first vertebra (400) in FIG. 7B, having holes (412, 414) adapted to receive the cable (408). The intermediate vertebrae (402, 404) each have four holes for receiving and passing along the cable (408). The groups of four holes (416, 418) for each of the intermediate vertebrae (402, 404) are illustrated in FIG. 7B. Alternatively, separate loops of a plurality of cables may be used in place of a single cable as described.

Figure 7D:
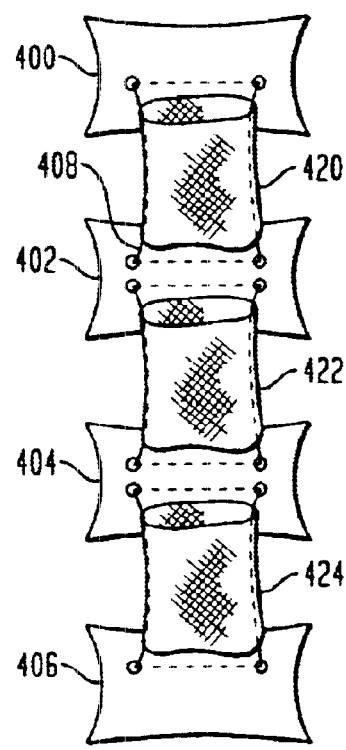
FIG. 7D is a schematic illustration of a plurality of vertebrae secured to each other with a cord and a plurality of flexible patches in accordance with the present invention.

As illustrated in FIG. 7D, a series of patches (420, 422, 424) of the type above-described may be implemented with the cable (408) between the adjacent vertebrae (400–406) in order to provide controlled tension therebetween. As described above with respect to FIG. 5C and FIG. 6C, the patches may be provided with material properties or coatings to enable specific functions such as the slow release of a substance contained therein, or to provide a barrier.

Figure 8:
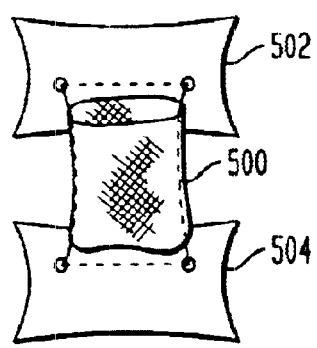
FIG. 8 is a schematic illustration of adjacent vertebrae secured to each other with a flexible patch according to the present invention.

Referring to FIG. 8, another embodiment of the present invention utilizes patches (500) of the type described above to span adjacent vertebrae (502, 504) without the use of a cable of any kind. This is achieved by anchoring the patch (500) by known bone anchoring means in a manner so that a desired tension is achieved. As illustrated in FIG. 8, the patch (500) may be anchored at its four corners.

It is contemplated that the above-described embodiments may be implemented without the use of a fusion device. For example, the present invention may be used with artificial disc or nucleus implants or no implants at all. The shape of the patch may be varied to achieve desired tension or ease or insertion. The location of the knot or crimp described above may be varied to occur between vertebral bodies or at a vertebral body, with the intention of locating it out of the way of any tissues or blood vessels that may be damaged by it while enabling convenient installation.

Figure 9A:
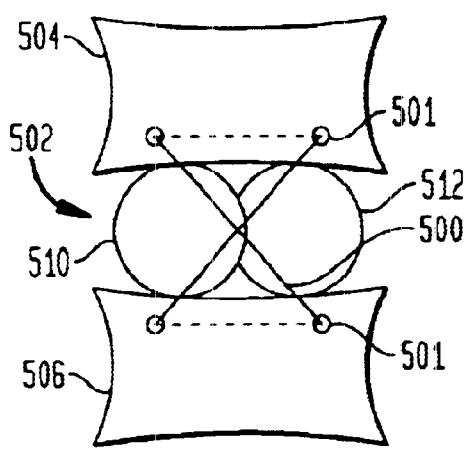
FIG. 9A is schematic view of a cord component of the present invention secured to and crossing over itself between two bone structures.
Figure 9B:
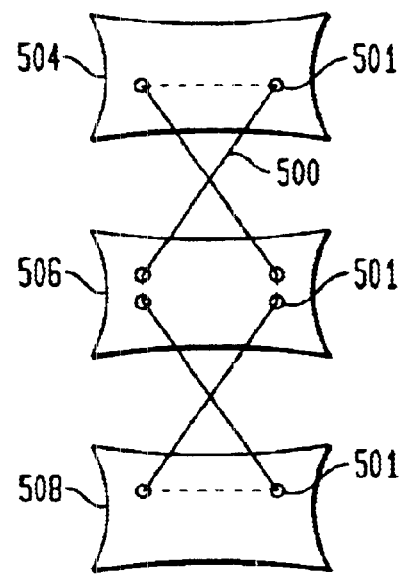
FIG. 9B is a schematic illustration of a pair of vertebrae secured to each other with a cord in accordance with the present invention, whereby the cord is crossed over itself between the adjacent vertebrae.
Figure 10A:
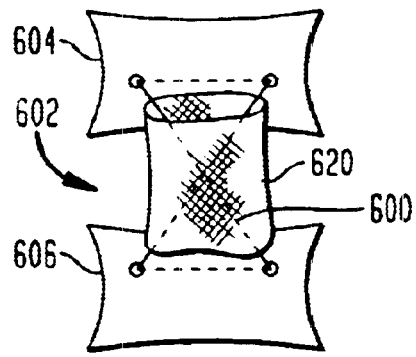
FIG. 10A is a schematic illustration of adjacent vertebrae secured to each other with a flexible patch according to the present invention, wherein the cord supporting the patch is crossed over itself between the vertebrae.
Figure 10B:
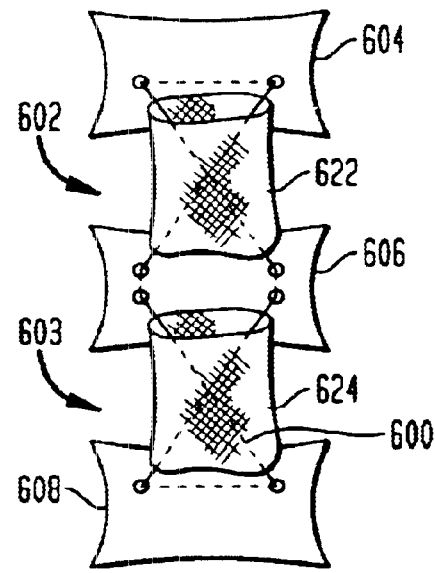
FIG. 10B is a schematic illustration of a plurality of vertebrae secured to each other with a cord in accordance with the present invention, whereby the cord is crossed over itself between the adjacent vertebrae.

If desired, the cord may be crossed over itself when spanning the disc space. For example, as shown in FIGS. 9A–9B, a cable (500) passing through holes (501) is crossed over itself diagonally when spanning a disc space (502) between adjacent vertebrae (504, 506) or a series of vertebrae (504, 506, 508). One or more fusion or other implant devices (510, 512) may be placed in the disc space (502). As shown in FIGS. 10A–10B, the cable (600) may be similarly crossed over itself when used in cooperation with a patch (620) or plurality of patches (622, 624) of the type disclosed herein in order to span one or more disc spaces (602, 603) between adjacent vertebrae (604, 606, 608).

While the preferred embodiments have been herein shown and described, it is understood that various modifications may be made without departing from the scope of the claimed invention. For example, the methods and configurations of tying the cable into a loop may employ a variety of knot or crimping methods, as well as a variety of tensioning methods. Further, the number of holes formed in bone structures to achieve the result of the present invention may be varied while maintaining sufficient and evenly distributed tension and support. Additional variations and modifications may be made. Lastly, while the preferred embodiment is described with respect to intervertebral fusion, it is not necessarily limited thereto and it is contemplated that the present invention may be used in other instances where orthopedic healing or fusion is required between adjacent or nearby bone structures.

What is claimed is:

1. A method of securing adjacent bone structures to each other while permitting a predetermined amount of relative movement therebetween, said method comprising:
    forming at least one hole on a first bone structure;
    forming at least one hole on a second bone structure;
    passing a folded cord through each of said holes, said cord having a first end comprising two free ends of the cord and second end comprising a folded end; and
    fixing two sections of the cord to each other to form a closed loop.

2. A method according to claim 1, wherein
    said two sections are fixed by forming a first loop on the second end, passing the first end through the first loop and drawing the first end until a desired tension in the cord is achieved, and forming a first half-hitch with the two free ends.

3. A method according to claim 2, further comprising forming a second half-hitch with the two free ends.

4. A method of securing adjacent vertebrae to each other while permitting a predetermined amount of relative movement therebetween, said method comprising:

forming a pair of holes on a first vertebra;

forming a pair of holes on a second vertebra;

passing a cord through each pair of said holes; and fixing two sections of the cord located near the ends of the cord to each other to form a closed loop.

5. A method according to claim 4, further comprising drawing the ends of said cord relative to each other in order to achieve a desired tension in the loop to be formed prior to the step of fixing the ends of the cord to each other.

6. A method according to claim 4, wherein said sections of the cord are fixed by tying them together.

7. A method according to claim 6, wherein said cord is crossed over itself at least between said first and second vertebrae.

8. A method according to claim 4, wherein prior to passing said cord through each of said holes, said cord is folded in half forming a first end comprising two free ends, and a second end comprising a folded end.

9. A method according to claim 8, wherein said two sections are fixed by forming a first loop on the second end, passing the first end through the first loop and drawing the first end until a desired tension in the cord is achieved, and forming a first half-hitch with the two free ends.

10. A method according to claim 9, further comprising forming a second half-hitch with the two free ends.

11. A method according to claim 4, wherein said cord is crossed over itself between said first and second vertebrae.

12. A method of securing adjacent bone structures to each other while permitting a predetermined amount of relative movement therebetween, said method comprising:

forming at least one hole on a first bone structure;

forming at least one hole on a second bone structure;

passing a cord through each of said holes and through securing means attached to a flexible patch; and fixing two sections of the cord located near the ends of the cord to each other to form a closed loop.

13. A method according to claim 12, further comprising drawing the ends of said cord relative to each other in order to achieve a desired tension in the loop to be formed by the cord and a desired tension in the flexible patch prior to the step of fixing the ends of the cord to each other.

14. A method according to claim 12, wherein said sections of the cord are fixed by tying them together.

15. A method according to claim 12, wherein prior to passing said cord through each of said holes, said cord is folded in half forming a first end comprising two free ends, and a second end comprising a folded end.

16. A method according to claim 15, wherein said two sections are fixed by forming a first loop on the second end, passing the first end through the first loop and drawing the first end until a desired tension in the cord is achieved, and forming a first half-hitch with the two free ends.

17. A method according to claim 16, further comprising forming a second half-hitch with the two free ends.

18. A method according to claim 12, wherein said securing means comprise a section of said flexible patch that is folded over to form a passage for said cord to pass therethrough.

19. A method according to claim 12, wherein said flexible patch is formed by a tube of flexible material and said securing means comprise the inside of said tube through which said cord is passed.

20. A system for securing adjacent bone structures to each other while permitting a predetermined amount of relative movement therebetween, said system comprising:

a cord forming a closed loop and being adapted to be secured to the adjacent bone structures such that said cord is tensioned; and a flexible patch secured to said cord at a plurality of points on said cord such that said patch is adapted to be tensioned between the bone structures.

21. A system according to claim 20, wherein said cord is securable to the bone structures by passing said cord through holes formed in the bone structures.

22. A system as in claim 20 wherein the adjacent bone structures are adjacent vertebral bodies.

23. A method of fusing adjacent bone structures, said method comprising positioning a bone fusion implant device between said adjacent bone structures;

forming at least one hole on a first bone structure;

forming at least one hole on a second bone structure;

passing a cord through each of said holes; and fixing two sections of the cord located near the ends of the cord to each other to form a closed loop.

24. A method according to claim 23, further comprising drawing the ends of said cord relative to each other in order to achieve a desired tension in the loop to be formed prior to the step of fixing the ends of the cord to each other, such that said tension in said loop contributes to compressive force applied to said implant device by said adjacent bone structures.

25. A method according to claim 23, wherein said sections of the cord are fixed by tying them together.

26. A method according to claim 23, wherein prior to passing said cord through each of said holes, said cord is folded in half forming a first end comprising two free ends, and a second end comprising a folded end.

27. A method according to claim 26, wherein said two sections are fixed by forming a first loop on the second end, passing the first end through the first loop and drawing the first end until a desired tension in the cord is achieved, and forming a first half-hitch with the two free ends.

28. A method according to claim 27, further comprising forming a second half-hitch with the two free ends.

29. A method of fusing adjacent vertebrae, said method comprising positioning a bone fusion implant device between said adjacent vertebrae;

forming at least one hole on a first vertebra;

forming at least one hole on a second vertebra;

passing a cord through each of said holes; and fixing two sections of the cord located near the ends of the cord to each other to form a closed loop.

30. A method according to claim 29, further comprising drawing the ends of said cord relative to each other in order to achieve a desired tension in the loop to be formed prior to the step of fixing the ends of the cord to each other, such that the tension in said loop contributes to compressive force applied to said implant device by said adjacent vertebrae.

31. A method according to claim 29, wherein
said sections of the cord are fixed by tying them together.

32. A method according to claim 29, wherein
prior to passing said cord through each of said holes, said cord is folded in half forming a first end comprising two free ends, and a second end comprising a folded end.

33. A method according to claim 32, wherein
said two sections are fixed by forming a first loop on the second end, passing the first end through the first loop and drawing the first end until a desired tension in the cord is achieved, and forming a first half-hitch with the two free ends.

34. A method according to claim 33, further comprising forming a second half-hitch with the two free ends.

35. A method of fusing adjacent vertebrae, said method comprising:
positioning a bone fusion implant device between said vertebrae;
forming at least one hole on a first vertebra;
forming at least one hole on a second vertebra;
passing a cord through each of said holes and through securing means attached to a flexible patch; and
fixing two sections of the cord located near the ends of the cord to each other to form a closed loop.

36. A method according to claim 35, further comprising drawing the ends of said cord relative to each other in order to achieve a desired tension in the loop to be formed by the cord and a desired tension in the flexible patch prior to the step of fixing the ends of the cord to each other, such that the tension in said loop and said patch contributes to compressive force applied to said implant device by said adjacent vertebrae.

37. A method according to claim 35, wherein
said sections of the cord are fixed by tying them together.

38. A method according to claim 35, wherein
prior to passing said cord through each of said holes, said cord is folded in half forming a first end comprising two free ends, and a second end comprising a folded end.

39. A method according to claim 38, wherein
said two sections are fixed by forming a first loop on the second end, passing the first end through the first loop and drawing the first end until a desired tension in the cord is achieved, and forming a first half-hitch with the two free ends.

40. A method according to claim 39, further comprising forming a second half-hitch with the two free ends.

41. A system for fusing adjacent bone structures, said system comprising:
a fusion implant device adapted to be positioned between the adjacent bone structures;
a cord securable to the adjacent bone structures such that said cord is tensioned; and
a flexible patch secured to said cord at a plurality of points on said cord such that said patch is adapted to be tensioned between the bone structures in a manner in which compressive force is applied to said implant device by the adjacent bone structures.

42. A system according to claim 41, wherein
said cord forms a closed loop and is securable to the bone structures by passing said cord through holes formed in the bone structures.

43. A system as in claim 41 wherein the adjacent bone structures are adjacent vertebral bodies.

44. A method of fusing adjacent bone structures, said method comprising
placing a fusion implant device between said adjacent bone structures; and
securing a flexible patch to at least two points on each of said adjacent bone structures in a manner in which said patch is tensioned therebetween, contributing to compressive force applied to said implant device by said flexible patch.

45. A method according to claim 44, further comprising
securing bone graft material to said patch such that said patch holds said bone graft material in a location between said adjacent bone structures.

46. A method of securing a plurality of adjacent vertebrae to each other in a manner permitting a predetermined amount of relative movement therebetween, said method comprising
forming at least one hole on a first vertebra;
forming at least one hole on a second vertebra;
forming at least one hole on a third vertebra;
passing a cord through each of said holes;
drawing the ends of the cord to each other to create tension in said cord; and
securing said cord ends in order to form a closed loop while maintaining tension therein.

47. A method of securing a plurality of adjacent vertebrae to each other in a manner permitting a predetermined amount of relative movement therebetween, said method comprising
forming at least a pair of holes on a first vertebra;
forming at least a pair of holes on a second vertebra;
forming at least a pair of holes on a third vertebra;
passing a cord through each of said holes;
drawing the ends of the cord to each other to create tension in said cord; and
securing said cord ends in order to form a closed loop while maintaining tension therein.

48. A method according to claim 47, wherein
prior to passing said cord through each of said holes, said cord is folded in half forming a first end comprising two free ends, and a second end comprising a folded end.

49. A method according to claim 48, wherein
said two sections are fixed by forming a first loop on the second end, passing the first end through the first loop and drawing the first end until a desired tension in the cord is achieved, and forming a first half-hitch with the two free ends.

50. A method according to claim 49, further comprising forming a second half-hitch with the two free ends.

51. A method of securing a plurality of adjacent vertebrae to each other in a manner permitting a predetermined amount of relative movement therebetween, said method comprising
securing a first flexible patch to at least two points on each of a first vertebra and a second vertabra in a manner in which said first patch is tensioned therebetween; and
securing a second flexible patch to at least two points on each of said second vertebra and a third vertebra in a manner in which said second patch is tensioned therebetween.

52. A system for securing adjacent bone structures to each other while permitting a movement therebetween, said system comprising
- a cord capable of being secured to the adjacent bone structures;
- a flexible patch secured to said cord at a plurality of points on said cord, said cord and said patch capable of applying a force tending to bring the adjacent bone structures toward each other when said cord is secured to the bone structures.

53. A system according to claim 52, wherein
said cord is securable to said bone structures by passing said cord through pre-drilled holes in the adjacent bone structures.

54. A system according to claim 52 further comprising
a fusion implant device for insertion between said adjacent bone structures.

55. A system according to claim 52 wherein said adjacent bone structures are adjacent vertebral bodies.

* * * * *